United States Patent [19]

Thomas

[11] 4,228,136
[45] Oct. 14, 1980

[54] LENS HOLDER AND STERILIZER

[75] Inventor: Michael D. Thomas, Arab, Ala.

[73] Assignee: Ryder International Corporation, Hanover Park, Ill.

[21] Appl. No.: 877,671

[22] Filed: Feb. 14, 1978

[51] Int. Cl.² .................... A61L 3/00; B05D 81/24
[52] U.S. Cl. .................... 422/307; 206/5.1; 219/385; 219/432; 219/433; 219/441
[58] Field of Search ............ 219/385, 386, 432, 433, 219/441, 442, 521; 134/117, 166 R, 201; 206/5.1, 815; 422/307, 300

[56] References Cited
U.S. PATENT DOCUMENTS

| | | | |
|---|---|---|---|
| 3,403,714 | 10/1968 | Hulm | 206/815 X |
| 3,695,280 | 10/1972 | Sturgeon | 206/5.1 |
| 3,801,278 | 4/1974 | Wagner et al. | 422/300 X |
| 3,908,111 | 9/1975 | Du Bois et al. | 219/433 X |
| 3,983,362 | 9/1976 | Hoogesteger et al. | 219/521 |
| 3,990,579 | 11/1976 | Manning | 206/5.1 |
| 3,998,590 | 12/1976 | Glorieux | 422/307 X |
| 4,080,167 | 3/1978 | Beers | 219/385 |
| 4,091,917 | 5/1978 | Clawson et al. | 206/5.1 |

FOREIGN PATENT DOCUMENTS 1051578 12/1966 United Kingdom .................... 219/521

Primary Examiner—Arnold Turk
Attorney, Agent, or Firm—Trexler, Wolters, Bushnell & Fosse, Ltd.

[57] ABSTRACT

A lens case for use with a dry heat sterilizer unit, or the like, wherein said sterilizer unit includes a substantially flat heated support surface with the lens case supportable thereon in intimate surface-to-surface heat conductive contact. The lens case is substantially flat and includes shallow, cup-like base and cover sections. The lens case base section includes separate, lens supporting arrangements for receiving a pair of lenses, said lens support arrangements being provided in side-by-side relation. The lens case is designed to be positioned on said support surface of said sterilizer unit only in an inverted position, i.e. with the cover engaged with said heated support surface, and said lens support arrangements inverted, which serves to prevent overheating of the lenses. Further, the cover member for the lens support arrangements, include central apertures, which permit the lenses to be engaged during opening of said covers, to preclude said lenses from adhering to said cover members.

14 Claims, 11 Drawing Figures

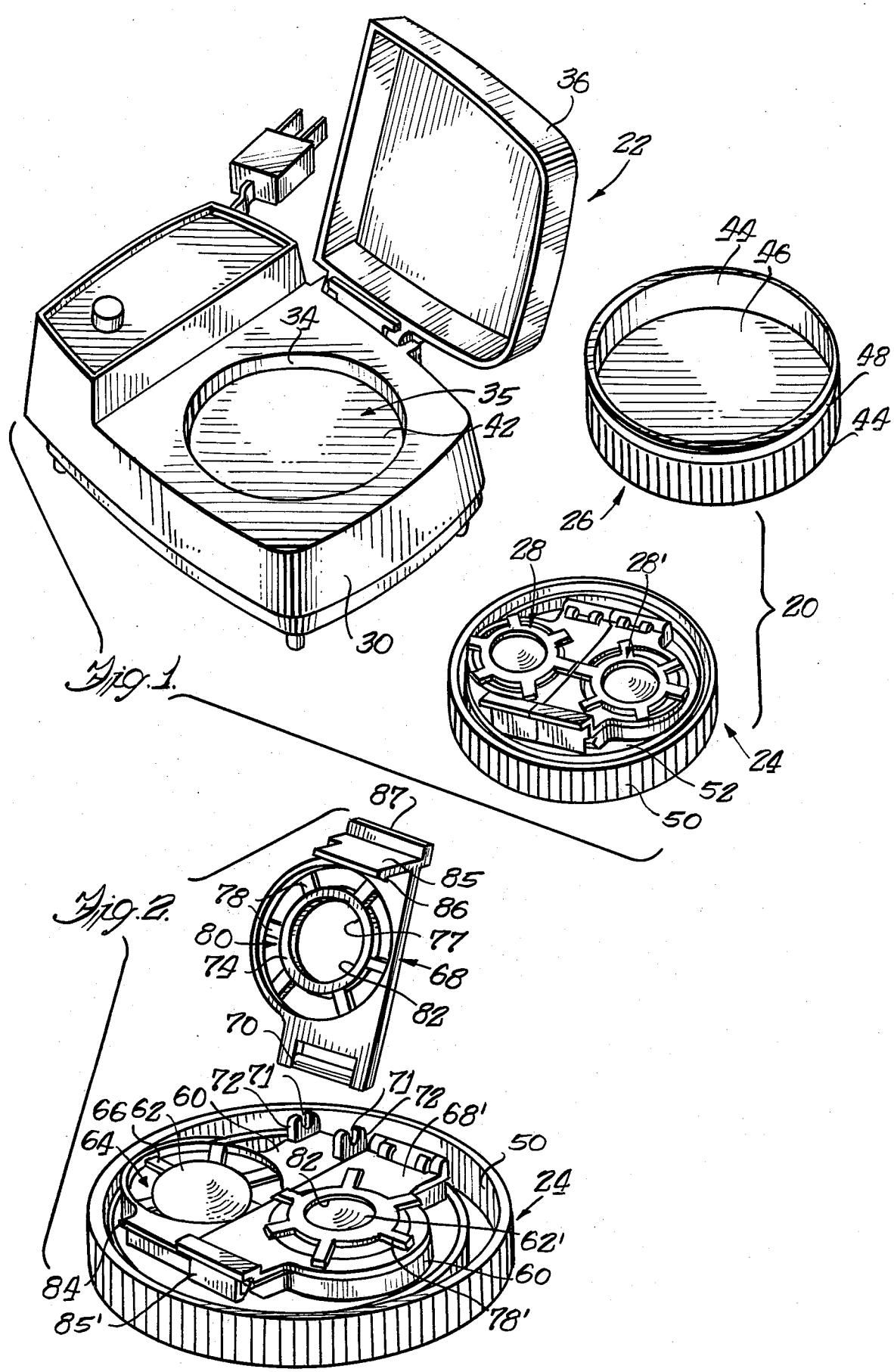

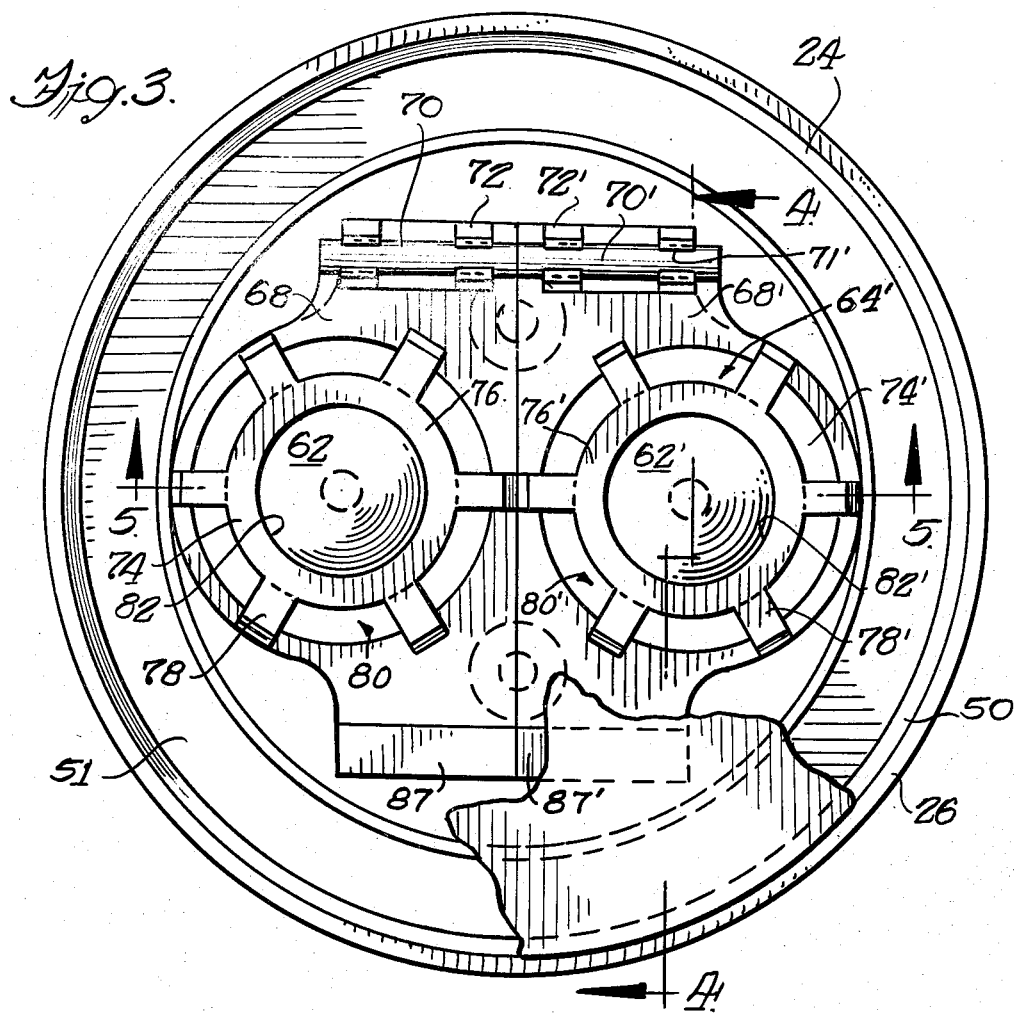
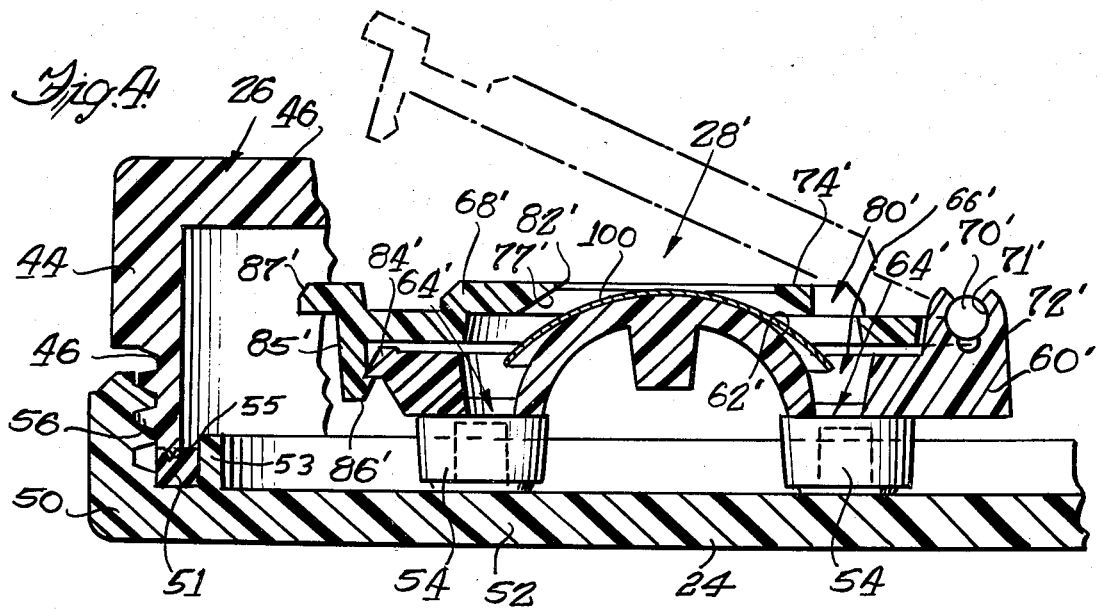

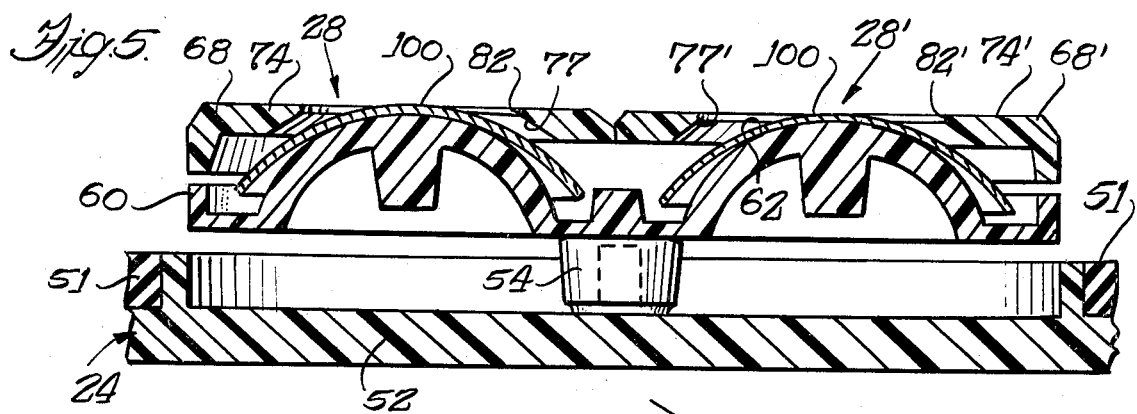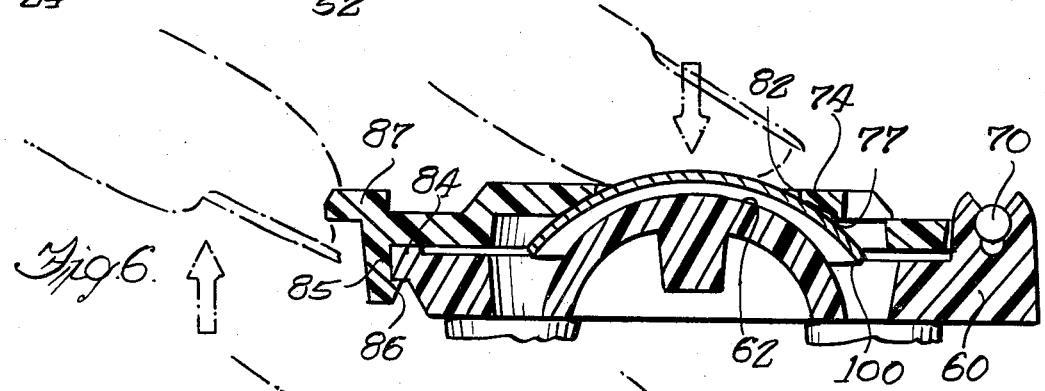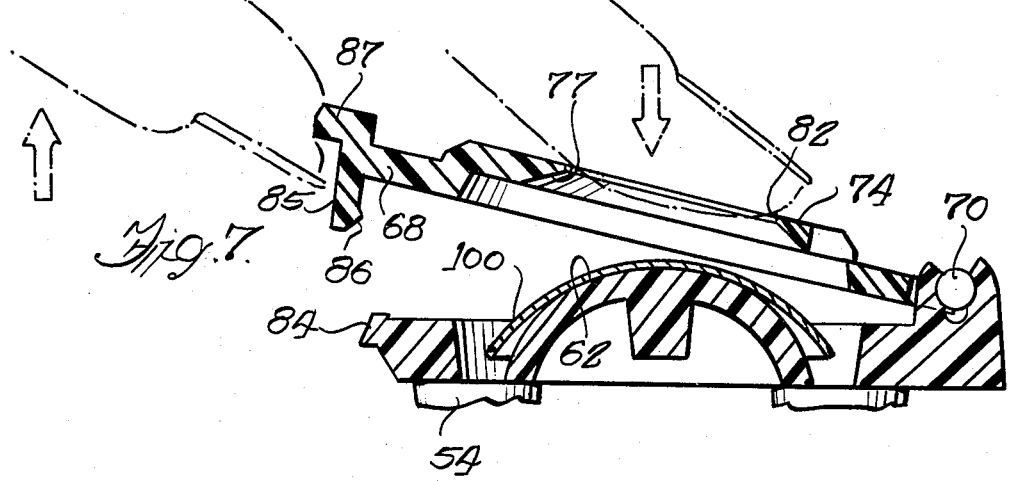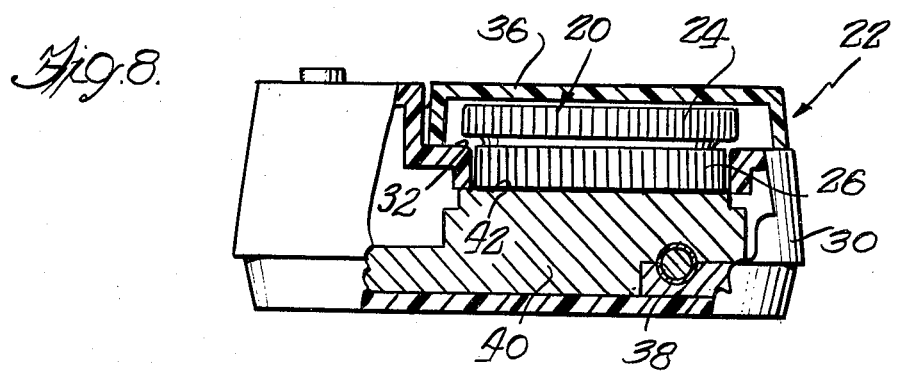

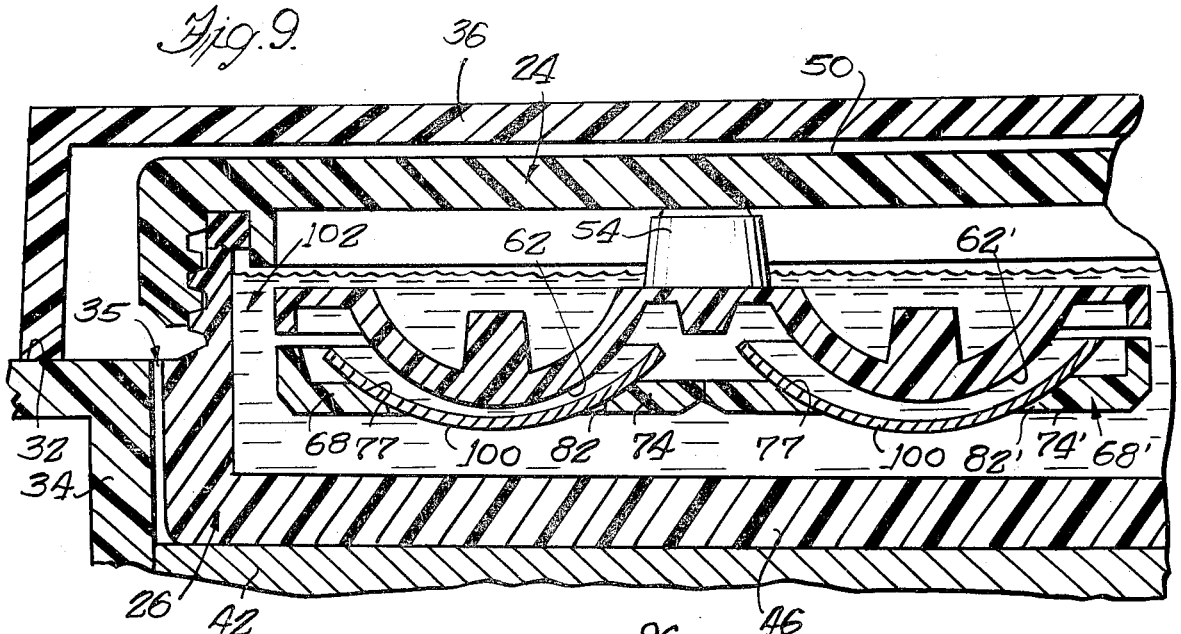
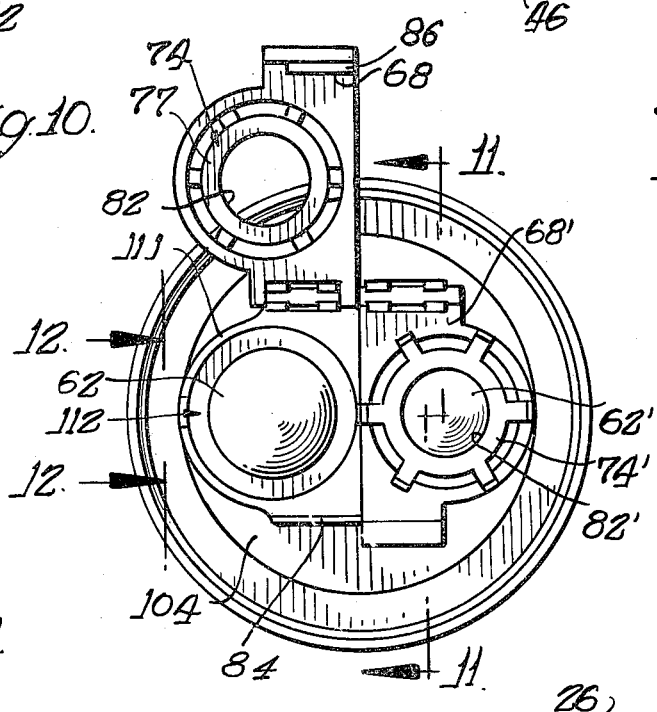
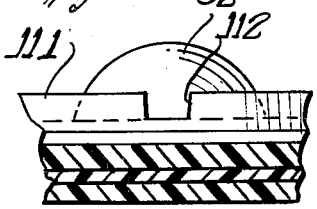
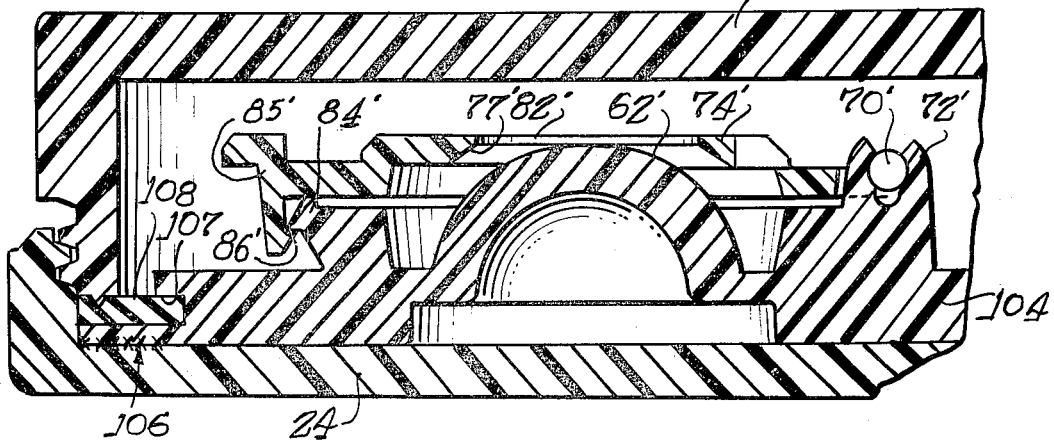

LENS HOLDER AND STERILIZER

BACKGROUND OF THE INVENTION

The present invention relates to a lens case for storing, cleaning and/or sterilizing a pair of contact lenses, and more particularly to a lens case which provides for mounting of the contact lenses in side-by-side relation, and is designed to facilitate removal of the lenses as well as to insure against overheating of the lenses during sterilization.

Until recently only contact lenses of a relatively hard nature were available, and while these required cleaning, sterilization was not a significant problem. There has now been developed a soft contact lens manufactured from a hydrophilic plastic material; i.e., a relatively porous plastic material that will absorb water, and upon doing so becomes soft and pliable. While hard lenses must be cleaned and sterilized periodically, the need for sterilization with respect to soft lenses is more acute, due to the relatively porous nature of the plastic nature which provides a medium for bacteria. As such soft contact lenses must be effectively cleansed or sterilized on a regular basis, preferably daily.

Two sterilization methods have been developed and approved for use with soft lenses. The first and most popular involves the disposition of the lenses in a saline solution, and the heating of the saline solution to a temperature sufficient to destroy any bacteria that might be present. The other method, employs the use of a chemical process to destroy the bacteria and thereby achieve sterilization. With regard to heat sterilization, this is accomplished either by a "wet heat" type sterilizing process, or a more recently developed "dry heat" process. With respect to the former, the lenses are placed in a case which includes the saline solution, and then the case is placed in a second vessel of water which is brought to the boiling point, the heat being transferred to the sterilizing case by way of the surrounding water. With the "dry heat" method of sterilization, the lenses are disposed within a case and the saline solution added, and the case is placed in direct contact with the heater, such that there is direct application of heat to the surface of the container and from there to the sterilizing solution.

The use of hard and soft lenses has resulted in the development of a number of prior art type lens cases, examples of which are shown in U.S. Pat. Nos. 3,770,113; 3,977,517; and 4,009,777. These prior designs, however, while suitable for wet heat sterilization, are not well adapted for use with the dry heat type of sterilization. As will become clear from the discussion to follow, the lens case of the present invention was designed with the problems attendent with dry heat sterilization in mind, and to avoid these problems. While the lens case of the present invention was developed primarily for use with dry heat sterilization, the design includes a number of structural and operational features which are advantageous regardless of whether the case is used to store hard lenses, or is used in a wet heat type of sterilization process. More specifically, the lens case of the present invention is designed to accommodate the lenses in a horizontally disposed side-by-side relation in a relatively shallow casing structure. The casing structure is horizontally elongate, thereby providing a large surface area for engagement with a heating element. Further, the lens case is designed for inverted positioning of the lenses with respect to the heater unit. More specifically, the lenses are carried by a supporting arrangement affixed to the base of the case, such that when the base and cover are engaged to close the case, the lenses are spaced from the wall section of the cover. In use, the case is inverted so that the planar surface of the cover is in direct engagement with the heating element rather than the base. This feature has a specific advantage, in that the path for direct heat conduction through the case from the heater to the lens is lengthened appreciably. Accordingly, the most direct path for heat transfer to the lenses is via the sterilizer solution which is what is desired. Accordingly, with this arrangement it is assured that the sterilizing solution will be heated to a desired temperature before any overheating of the lenses can occur. Without the inverted mounting, the planar wall surface of the base would be in direct contact with the heater unit. It can be appreciated that with this arrangement a direct path of heat transfer exists from the heater to the lenses via the base structure, and as such portions of the lenses which engage the structure may be overheated, resulting in the possibility of damage to the lenses.

Another problem which is obviated to a great degree by the present invention is the removal of the lenses from the lens case. With the prior art type cases such as illustrated in U.S. Pat. Nos. 3,977,517 and 3,770,113, there is employed a stationary, convex support surface for the lenses and a pivotally mounted cover which overlies said support surface. After sterilization and upon opening of the covers, it is not uncommon for the lenses to adhere to the cover. When this occurs, the user may experience difficulty in locating the lens, and when located, it thus becomes necessary that the user contact or engage the inner or concave lens surface with his or her finger, in order to remove the lenses from the cover. This contact can often lead to contamination of the inner lens surface which is that surface engaged against the eye. Thus, the act of removal of the lens from the sterilizing case can negate that which was accomplished by the sterilizing procedure.

With the present invention, as will be discussed in detail hereinafter, there is provided a structure which enables a user to disengage the lenses from the cover structure, and insure that they will remain disposed upon the convex support surface upon opening of the cover structure. The user then need only contact the outer or convex lens surface in placing the lens on the eye, avoiding all contact and possible contamination with the inner lens surface. As an additional matter, it will be appreciated that the lens are relatively clear, and are not always easy to locate for removal from the case. This fact coupled with the prior art designs which employ oppositely mounted support structures, have contributed to the loss of numerous lenses. With the present invention, the lenses are mounted in side-by-side relation, with the lens covers opening in the same direction. This side-by-side mounting coupled with the structure to prevent adherence of the lenses to the cover greatly facilitate removal of the lenses, without the danger of loss or contamination thereof.

DESCRIPTION OF THE DRAWINGS

With the above in mind, attention is now directed to the drawings wherein the present invention is illustrated as follows:

FIG. 1 is a perspective view of a sterilizer unit and a lens case constructed in accordance with the present invention;

FIG. 2 is a enlarged perspective view of the base portion of the lens case of FIG. 1, with one of the cover members disengaged from its pivotal mounting;

FIG. 3 is a top plan view of the base portion of FIG. 2;

FIG. 4 is a partial sectional view taken along the line 4—4 of FIG. 3;

FIG. 5 is a partial sectional view taken along the line 5—5 of FIG. 3;

FIGS. 6 and 7 illustrate the manner of employing the lens case of the present invention to insure that the lens remains on the convex support surface during opening of the cover structure;

FIG. 8 is a partial sectional view showing the lens case mounted within the heating well of the sterilizer unit, with the case in the inverted position;

FIG. 9 is a partial sectional view taken through the lens case when mounted in the heating well of the sterilizer unit and illustrating the disposition of the lenses when the lens case is in the inverted position;

FIG. 10 is a top plan view of a lens case constructed in accordance with a modified form of the invention;

FIG. 11 is a partial sectional view taken along the line 11—11 of FIG. 10 but illustrating the cover structure in engagement with the base portion;

FIG. 12 is a partial sectional view taken along the line 12—12 of FIG. 10.

DESCRIPTION OF THE ILLUSTRATED EMBODIMENTS

The lens case of the present invention is designated generally 20, and is illustrated in FIG. 1 in conjunction with one form of sterilizer or heating unit 22 that may be employed therewith. The lens case 20 is comprised of a base portion 24, and a cover portion 26 adapted to be engaged with said base portion to provide a sealed container for the sterilizing solution and lenses. Both the base portion 24 and the cover portion 26 are of a relatively shallow, cup-like construction, with the base portion 24 including separate supporting arrangements for the lenses, designated generally 28 and 28'; the specific construction of which will be discussed in greater detail hereinafter.

With respect to the sterilizer or heating unit 22, attention is directed to FIG. 8 in conjunction with FIG. 1. As can be seen, the sterilizer unit 22 includes an outer casing structure 30 having an upper surface portion 32 in which there is provided an aperture defined by an inwardly turned annular flange portion 34, which partially defines a heating well 35 for the case 20. Pivotally mounted with respect to the casing surface 32, is a cover section 36 adapted to overlie the heating well 35 and a lens case 20 disposed therein. Interiorly of the casing 30, there is provided a conventional form of heater arrangement, which includes (note FIG. 8) a resistance type heater 38 mounted in engagement with the metallic heating block 40.

The heating block 40 includes a substantially flat upper surface 42 which is circumscribed by the aperture defined by the annular flange 34. Accordingly, said flange 34 and the surface 42 serve to define the heating well 35, with said surface 42 adapted to support the lens case 20 in surface-to-surface contact when said case is disposed in said well.

Before discussing the operational features of the lens case 20 when employed during sterilization, it is believed advantageous to consider first the overall construction of said case 20. Accordingly, attention is directed to FIGS. 2–5 which will be considered in conjunction with FIG. 1 relative to said case structure.

As noted above, the case 20 includes the cover 26 and the base 24 having the lens support arrangements 28 and 28' mounted to said base 24. The cover 26 is of a circular, shallow cup-like configuration including an upstanding annular side wall 44, and a planar wall portion 46. The side wall 44 is provided with an external thread 48 to facilitate connection of the cover 26 to the base 24. Base 24 is of a similar, cuplike design and includes an annular side wall portion 50 and a bottom wall portion 52. As is best seen in FIGS. 4 and 5, the lens support arrangements 28 and 28' are mounted to the bottom wall 52 in spaced relation with respect to said bottom wall 52, by a number of posts or standards 56. The annular side wall 50 is provided with an internal thread 56 adapted for mating engagement with the external thread 46 on the cover. As is best seen in FIG. 4, base 24 includes an annular gasket 51 disposed in a groove defined by an annular wall 53 and the base side wall portion 50. Accordingly, when the cover 26 and base 24 are engaged, the end face 55 of cover side wall 44 will engage the gasket 51 to provide a fluid tight seal.

With respect to the mounting arrangements 28 and 28' employed with the illustrated embodiments of the invention, these are substantially identical, except for the cover members which as can be seen, are mirror image parts. For purposes of description, only the support arrangement 28 illustrated in the left-hand portion of FIG. 2, as viewed, will be discussed in detail. It is to be understood that the elements or components of the companion support arrangement 28' are virtually identical, and these will be designated by the same reference characters, primed (').

Basically, the support arrangements 28 includes a stationary segment 60 to which the posts 54 are connected. Stationary segment 60 is provided with a pair of convex lens support surfaces 62 and 62', surrounded by a plurality of openings designated generally 64; 64', which openings are defined by the webs or arms 66; 66' which serve to connect the convex support surfaces 62; 62' to the main portion of the stationary segment 60. A cover member 68; 68' is provided, which cover member includes means for pivotal mounting thereof to the stationary segment 60. More specifically, the cover member 68; 68' includes a rod-like portion 70; 70' that is adapted to be engaged with a snap fit in the circular recesses 71; 71' provided in the journal flanges 72; 72'. The rod-like portion 70; 70' is then free to rotate with respect to the flange 72; 72', permitting the cover member 68; 68' to be pivoted between an open position (phantom outline in FIG. 4) and a closed position (shown in full line). The cover member 68; 68' further includes a concave portion 74; 74' adapted to overlie in spaced relation, the convex lens support surfaces 62; 62'. The concave portion 74; 74' of the cover 68; 68' is defined by a matrix which includes an annular segment 76; 76' having a concave inner surface portion 77; 77', said annular segment being connected to the main portion of the cover by arms or webs 78; 78'. As can be seen, the arms 78; 78' are spaced so as to define openings 80; 80' with the annular segments 76, 76' providing an enlarged, central opening 82; 82'.

The stationary segment 60 and cover 68; 68' include means to maintain said cover in the closed position against inadvertent opening, with said means permitting the covers to be easily disengaged and pivoted to the open condition. More specifically, the above-mentioned means are provided by a further snap-fit arrangement which includes a ledge 84; 84' on the stationary segment 60, and a resilient flange 85; 85' on the end of the cover 68; 68' opposite the rod-like segments 70; 70'. The resilient flange 85; 85' includes a lip 86; 86' adapted to be engaged over the ledge 84; 84' provided on the stationary segment 60. Cover 68; 68' also includes a tab portion 87; 87' which facilitates manual engagement of the cover, such that is may be pivoted upwardly towards the open position (as shown in dotted outline in FIG. 4) to disengage the snap fit provided by lip 86; 86' and flange 84; 84'.

As can be appreciated from the above discussion and FIGS. 2 and 3, the respective convex lens portions 62; 62' are formed as an integral part of the stationary segment 60 and are in side-by-side disposition. The cover members 68 and 68' are separately operable and are pivotally mounted to the stationary segment 60 such that when said covers are closed they will overlie the convex support surfaces 62 and 62'. In the illustrated embodiment, the cover member 68; 68' are mirror image parts, this design being selected to minimize the spacing required between the respective convex support surfaces 62 and 62'. Accordingly, with the above in mind, attention will now be directed to the manner in which the lens case 20 is used.

When it is desired to use the case 20 to sterilize or store a pair of lenses, the cover 26 is removed, and the pivotally mounted members 68 and 68' are raised to the open position. As illustrated in FIGS. 4 and 5, the lens 100 are then placed on the convex support surfaces 62 and 62', with the inner or concave surface of the lens 100 engaged on said support surface and the cover members 68 and 68' are closed. Next, a quantity of sterilizing solution 102, usually a saline solution compatible with the chemistry of the eye, is placed within the cup-like cover portion 26, and the base 24 is inverted and secured to the cover.

It should be noted that the base 24 has a diameter or effective maximum dimension that is greater than that of the cover section 26. Correspondingly, the diameter or maximum dimension of the heater well 35 is sized such that it is less than the diameter of the base 24, but greater than the diameter of the cover portion 26 (this relationship is best illustrated in FIG. 9). Accordingly, the case 20 can be disposed in the heater well 35 only in the inverted position, viz., with the cover 26 engaged on surface 42, since the base portion 24 cannot pass inwardly of the well aperture 34.

With the lens case 20 positioned within the heater well 35, with cover 26 resting on heater block surface 42 the resistance heater 38 is activated to heat the heater block 40. As can be seen in FIG. 9, the wall portion 46 of the cover 26 is in extensive surface-to-surface contact with the upper surface 42 of the heater block 40. Thus, by the use of a shallow, horizontally elongate design for the base 24 and cover 26, an increased surface area is provided in engagement with the heater block, thereby maximizing the rate of heat transfer to the sterilizing solution 102. Of importance also, is the fact that in the inverted position of FIG. 9, the outer convex surface portions of lenses 100 will be supported on the concave surfaces 77 and 77' of covers 68 and 68'. As can be seen, this exposes the entire inner surface portion of said lenses 100 to the sterilizing solution 102. The various openings 64; 64', 80; 80', and 82; 82' in the covers 68 and 68' and the stationary portion 60 provide for the free flow of the sterilizing solution 102 about the lenses 100.

The sterilizer or heater unit 22 employs a conventional thermostat (not shown) that will deactivate the heater 38 once a predetermined temperature is reached. In dry heat sterilization, the temperatures involved are extremely high, normally in excess of 180° F. It will be appreciated that due to heat loss, the heater 38 and block 40, must be raised to temperatures well in excess of the desired sterilizing temperature for the liquid solution 102. Further with this fact in mind, it should be noted that soft lenses may be adversely affected by extreme heat, thus overheating of the lenses 100 must be prevented. Due to the inverted mounting of the casing 20, as discussed above, the design of the present invention tends to obviate to a great extent the danger of overheating. More specifically, it is believed that if or when overheating of the lenses occurs, with the prior art case designs, it is due to the transfer of heat directly to the lenses by way of the casing structure. By way of example, using the case 20 as discussed above, if the base portion 24 were disposed in engagement with the heater block 40, there is a distinct possibility that the rate of heat transfer to the casing will be faster than that to the sterilizing solution, such that the portions of the lenses in engagement with the casing structure might be overheated, before the thermostat deactivates the heating element. With the present invention and the inverted mounting arrangement discussed above, overheating of this nature is substantially eliminated.

More specifically, with the arrangement as illustrated in FIG. 9, the base 24 to which the lens arrangements 28 and 28' are mounted, is not in direct contact with the heater block 42, as only the cover 26 is so engaged. Accordingly, the path of heat transfer to the lenses 100 via the casing structure is extremely circuitous, and since the lenses 100 rest upon the concave surfaces 77 and 77', they are virtually suspended within the sterilizing solution 102. As such, there is little or no danger that hot spots will result in conjunction with the casing structure supporting the lenses 100, and overheating thereof is unlikely.

Once the sterilizing operation is completed, the lens case 20 should be allowed to cool before any attempt is made at removal of the lenses 100. Once cooled, the cover 26 is disengaged from the base 24, and the lenses 100 can be removed from the respective support arrangements 28 and 28'. A problem has been encountered with prior art designs at this stage, in that while it is desired that the lens will remain on the convex support surfaces upon opening of the cover members, quite often the lenses will adhere to the cover structure. When this occurs, it is necessary for the user to contact or touch the inner lens surface in order to remove it from said cover structure, with said contact giving rise to a possibility of contamination of said inner lens surface. Since the inner surface of the lens is that engaged against the eye, contamination during removal, may lead to an infection. As will now be discussed with regard to FIGS. 6 and 7, the design of the lens case 20 of the present invention permits the lenses 100 to be removed without the user touching the inner lens surface.

Looking to FIGS. 6 and 7, it will be recalled that the cover members 68 and 68' include enlarged openings 82 and 82'. These openings are sufficiently large to permit a portion of the outer convex surface of the lenses 100 to extend therefrom, as shown in FIG. 9, but are not of a size which will permit the lenses 100 to pass freely through said openings. Accordingly, during opening of the cover members 68 and 68', the user need only to position a finger over the opening 82 or 82' as illustrated in FIGS. 6 and 7, thereby dislodging the lens 100 from the cover structure 68 or 68' and insuring that the lens will be disposed upon the convex support surfaces 62 and 62' once the cover structure 68 or 68' has been opened. The user can now remove the lenses 100 and insert said lenses employing contact only with the outer convex portion of said lenses, thereby substantially reducing the possibility of contamination of the lenses, and the infection which may result therefrom.

In FIGS. 10-12, there is illustrated a modified form of the invention, which differs from that as discussed above only with regard to the design of the stationary segment to which the cover members 68 and 68' are pivotally mounted. Accordingly, where possible with regard to this embodiment, the prior reference characters employed above will be used to designate similar structure.

The lens case 20 of FIGS. 11-12 utilizes a cover portion 26 and a base 24 substantially identical to those as discussed above. The primary difference between this embodiment and that discussed above is the construction of the stationary segment 104 of the lens support arrangement 28 and 28'. More specifically, the stationary segment 104 is affixed directly to the bottom wall 52 of the base 24 by use of an annular ultrasonic weld, or the like, indicated at 106. In addition, the perimeter of the stationary member 104 is provided with an annular groove 107, as illustrated, in which is disposed an annular seal 108. The seal 108 is engaged by a lip 110 provided on the end face of the cover structure 26 when assembled, and also engages the side wall 50 of cover 24. Thus, it can be appreciated that the space disposed between the bottom wall 52 and the stationary element 104 is sealed.

Similar to the lens case design as discussed above with regard to FIGS. 1-9, the stationary element 104 includes a pair of convex lens support surfaces 62 and 62' formed integral therewith. Unlike the previously discussed embodiment, however, no openings are provided in said stationary element about said lens support surfaces, as it is intended that the space beneath said stationary element 104 is to remain sealed. Disposed about each said lens support surface 62 and 62' there is provided an upstanding flange 111 which includes one or more gates or openings 112 (see FIG. 12) which facilitate the flow of sterilizing solution about the convex support surfaces 62 and 62'. In conjunction with each said convex support surface 62 and 62', there is provided a cover member 68 and 68', respectively, of identical construction to that as discussed previously. As such, the cover structure and the convex support surfaces provide as stationary element 104 functioning in the identical manner discussed above. As such, further discussion concerning the structural features of this embodiment and its operation are not deemed necessary.

From the above discussion, it is believed clear that the primary difference in the lens case of FIGS. 10-12, with respect to that as discussed with regard to FIGS. 1-9, is that the space between the stationary member 104 and the bottom wall 52 of the base portion is sealed. As such, contaminants and residue which may result from the repeated sterilization operation cannot build up therein, and the case is easily cleaned.

The present invention is believed adequately described in connection with the preferred embodiment illustrated in the drawings and discussed above. It is to be understood that it is not intended that said invention be limited to the specific embodiments illustrated, as it is contemplated that those skilled in the art may bevise various alternatives, modifications and/or equilalents as may be included within the spirit and scope of the invention, which are defined by the claims appended thereto.

The invention is claimed as follows:

1. A generally flat, horizontally elongate lens case for housing a pair of contact lenses in side-by-side relation and adapted for use with a sterilizer unit including a heating well for receiving the case and a heater support surface upon which the lens case will rest, said lens case comprising a base section and a cover section, means on said base and cover sections for affixing one to the other to define the assembled condition for said case and provide an enclosed space for a sterilizing solution, said base section including separate, side-by-side lens support arrangements, each for receiving one of a pair of lenses, each said lens support arrangement including a convex support surface facing outwardly of said base section and adapted to have a lens supported thereon with the concave surface of the lens engaging said convex support surface, and a concave cover member adapted to overlie said convex support surface in spaced relation thereto to retain a lens therebetween, said cover members including aperture means for permitting the flow of sterilizing solution to the lenses, such that both said lenses will be oriented in the same manner with respect to said base section, and means on said lens case permitting only said cover section to be received in said sterilizing unit heating well and engaged with said heater support surface, thus insuring that when said lens case is disposed in said heating well, the contact lens support means will be disposed in an inverted position, with said inverted position permitting said lenses to be supported on the concave cover members, so that the concave surfaces of the lenses will be exposed directly to the sterilizing solution, and the length of the heat transfer path through the case material is maximized thereby to prevent against the possibility of overheating of the lenses.

2. A lens case construction according to claim 1 wherein said means to permit only inverted mounting includes said base section having an effective maximum diameter larger than that of the heating well while said cover section has an effective diameter sized such that only said cover member can be received in said heating well.

3. A lens case according to claim 1, wherein said cover member includes an opening of sufficient size to permit a portion of the convex surface of the lens to extend therefrom should the lens adhere to said cover member, said opening being smaller than the effective diameter of said lens so that said lens will not inadvertantly pass therethrough, such that during opening of the cover member to remove a lens, a user may engage the convex surface of a lens which may have adhered to said cover member, thus displacing said lens from said cover structure and insuring that said lens will be disposed on said convex support surface upon opening of said cover structure.

4. A lens case according to claim 1, wherein said base and cover section are of a shallow cup-like configuration to provide a case having a horizontal dimension which is substantially greater than its vertical dimension.

5. A lens case according to claim 1 wherein both said base and cover sections are of a circular, shallow cup-like construction, the diameter of said base section being greater than that of the cover section and sized to be greater than that diameter of the sterilizer unit heating well, such that the sizing of said base section provides the means permitting only the cover section to be disposed in said well.

6. The combination as recited in claim 1, wherein said lens support arrangement is provided by a disc-like member disposed within said base section, said base section having a bottom wall, and said disc-like member being integrally affixed to the bottom wall of said base about the periphery thereof to seal the space between said disc-like member and the bottom wall of said base section, said disc-like member including a raised, flange-like portion surrounding each said convex support surface, and gate means formed in said raised flange-like portion to facilitate the free flow of sterlizing solution.

7. In combination, a dry heat sterilizer unit for contact lenses, and a generally flat, horizontally elongate lens case for housing a pair of contact lenses in side-by-side relation and adapted for use with said sterilizer unit which includes a heating well for receiving the case and a heater support surface upon which the lens case will rest, said lens case comprising a base section and a cover section, means on said base and cover sections for affixing one to the other to define the assembled condition for said case and provide an enclosed space for a sterilizing solution, said base section including separate, side-by-side lens support arrangements, each for receiving one of a pair of lenses, each said lens support arrangement including a convex support surface facing outwardly of said base section and adapted to have a lens support thereon, with the concave surface of the lens engaging said convex support surface, and a concave cover member adapted to overlie said convex support surface in spaced relation thereto to retain a lens therebetween, said cover member including aperture means for permitting the flow of sterlizing solution to the lenses, such that both said lenses will be oriented in the same manner with respect to said base section, and means on said lens case and sterilizer unit permitting only said cover section to be received in said sterilizer unit heating well and engaged with said heater support surface, thus insuring that when said lens case is disposed in said heating well, the contact lens support means will be disposed in an inverted position, with said inverted position permitting said lenses to be supported on the concave cover members, so that the concave surfaces of the lenses will be exposed directly to the sterilizing solution, and the length of the heat transfer path through the case material is maximized thereby to prevent against the possibility of overheating of the lenses.

8. The combination as recited in claim 7, wherein said means for permitting mounting of the lens case to the support surface only in the inverted position, includes a housing for said sterilizer unit and a heating well formed in said housing, which heating well is partially defined by said heated support surface and aperture means provided by an inwardly turned lip portion, thus spacing the upper surface of said housing from said heated support surface, said aperture means having an effective dimension greater than the effective dimension of said cover section, but less than the effective dimension of said base section, such that the base section cannot be received within said heating well and only said cover section can be placed in surface-to-surface engagement with said heated support surface, thereby insuring the inverted mounting of said lens case.

9. The combination as recited in claim 7, wherein said cover member includes an opening in the area of said concave portion, said opening being of a size smaller than the effective diameter of said lenses, such that said lenses will be retained in the space defined by said cover and said support surface, said opening being sufficiently large to permit a portion of the convex surface of the lens to extend therefrom, such that upon opening of said cover a user may engage said convex lens surface of a lens which may have adhered to said cover to disengage and separate said lens from the cover, thus insuring that the lens will remain on the convex support surface upon opening of the cover member.

10. A lens case for a pair of contact lenses adapted for use in the storage, cleaning, sterilization or the like, of said lenses, said case comprising separate contact lens supporting arrangements, at least one of said arrangements being comprised of, a convex support surface for a lens, a cover member pivotally mounted with respect to said convex support surface and including a concave portion, said cover member being movable between an open and a closed position such that when in the closed position the concave portion thereof will overlie said convex support surface in spaced relation with respect thereto, providing a space within which a lens may be disposed for storage, cleaning, sterilization or the like, said concave portion of the cover member including an opening disposed generally central thereof and of sufficient size to permit a portion of the convex surface of the lens to extend into said opening should the lens adhere to said cover member, said opening being smaller than the effective diameter of said lens so that said lens will not inadvertently pass therethrough, such that during opening of the cover member to remove a lens, a user may prevent the lens from adhering to the cover by placing a finger over said opening thereby engaging the convex surface of a lens which may have adhered to the cover member, and thereby displacing said lens from said cover structure, thus insuring that said lens will be disposed on said convex support surface upon opening of said cover structure.

11. A lens case according to claim 10, wherein said case includes substantially shallow cup-like base and cover portions, with means provided thereon to interconnect said base and cover portions to provide a sealed container with said separate contact lens supporting arrangements carried internally thereof by one of said base or cover portions.

12. A lens case according to claim 10, wherein said separate lens supporting arrangements are of a similar construction, and are disposed in side-by-side relation with the respective cover members opening in the same direction.

13. A case according to claim 10, wherein said separate contact lens supporting arrangements are carried by said base portion, and said base portion has an effective maximum lateral dimension greater than that of said cover portion such that said case may be employed with a sterilizer unit having a heating well sized to receive only said cover portion, thereby insuring inverted mounting of said lens case device when disposed in said well.

14. A case according to claim 10, wherein said lens supporting arrangements includes a plurality of openings surrounding said convex support surface; said lens supporting arrangements being mounted to the bottom wall of said base portion by at least one post element thereby spacing said lens support arrangements from said bottom wall to facilitate the free flow of any solution in the case about said lenses.

* * * * *